United States Patent [19]

Hunt et al.

[11] 4,265,847

[45] May 5, 1981

[54] TABLETTING PROCESS

[75] Inventors: Peter Hunt; Aston M. Trelford, both of Bury-St-Edmunds, England

[73] Assignee: Kirby Pharmaceuticals Ltd, Bury-St-Edmunds, England

[21] Appl. No.: 122,833

[22] Filed: Feb. 20, 1980

Related U.S. Application Data

[63] Continuation of Ser. No. 891,813, Mar. 30, 1978, abandoned.

[51] Int. Cl.³ .............................................. B29B 1/02
[52] U.S. Cl. ..................................... 264/122; 424/44
[58] Field of Search ........................... 264/122; 424/44

[56] References Cited

U.S. PATENT DOCUMENTS

| | | | |
|---|---|---|---|
| 2,985,562 | 5/1961 | Millard et al. | 424/44 |
| 4,093,710 | 6/1978 | Sass et al. | 424/44 |

FOREIGN PATENT DOCUMENTS

| | | |
|---|---|---|
| 1107824 | 3/1968 | United Kingdom . |
| 1165098 | 9/1969 | United Kingdom . |
| 1221038 | 2/1971 | United Kingdom . |
| 1241201 | 8/1971 | United Kingdom . |
| 1292820 | 10/1972 | United Kingdom ............... 424/44 |

OTHER PUBLICATIONS

Grant, J. "Hackh's Chemical Dictionary", McGraw-Hill Co., New York, 1969, p. 402.

*Primary Examiner*—Donald E. Czaja
*Assistant Examiner*—James R. Hall
*Attorney, Agent, or Firm*—Emory L. Groff, Jr.

[57] ABSTRACT

A direct compression process for forming an effervescent tablet containing an active chemical compound is enhanced by the addition to the composition to be compressed of an alkali metal carbonate.

1 Claim, No Drawings

TABLETTING PROCESS

This is a continuation of application Ser. No. 891,813 filed Mar. 30, 1978, now abandoned.

This invention relates to the preparation of chemical compositions and in particular to chemical compositions compounded in effervescent tablet form.

It is well known to produce effervescent chemical compositions in tablet form. Such compositions are water soluble comprising an active chemical compound, for example, a compound having sterilizing or bactericidal properties, medical or pharmaceutical activity, an alkali metal bicarbonate e.g. sodium or potassium bicarbonate and a solid aliphatic carboxylic acid such as citric acid, tartaric acid or adipic acid or an acid salt thereof. In use, such tabletted compositions are dissolved in water when the interaction of the bicarbonate and acid components results in the release of carbon dioxide, thus increasing the rate of solution of the components and producing a liquid in which the active ingredient is homogeneously dissolved.

The compositions may be tabletted by one of two manufacturing processes defined as follows:

1. Wet Granulation Process—In this procedure ingredients are mixed together usually in separate fractions and wetted with a solvent usually water. The wet mass is forced through a sieve to form granules which are then dried. The separate granule fractions are then mixed together and the granules compressed on a tablet press to form tablets.

2. Direct Compression Process—In this procedure, the ingredients in suitable powder form are mixed together without wetting and compressed on a tablet press to form tablets.

The direct compression process is desirable because it requires less labor and equipment time and therefore may be more economical than the wet granulation process. However, experience suggests that effervescent tablets produced by the wet granulation process have more desirable characteristics. Such tablets usually exhibit (1) greater hardness (2) superior physical appearance, and most importantly superior solution characteristics in that the tablet retains a unit form. Ingredient "fall out" is minimized and solution is achieved as effervescence proceeds. Thus, at the completion of effervescence complete solution has been accomplished apart from slight particulate residue when insoluble lubricants are used. Effervescent tablets commonly produced by direct compression methods usually disintegrate too rapidly resulting in "ingredient fall out" which is slow to disperse and dissolve.

It has now been found that the disadvantages experienced hitherto with the direct compression method may be substantially obviated by the addition of an alkali metal carbonate to the compositions prior to the tabletting process.

The inclusion of anhydrous alkali metal carbonates has also been shown to inhibit traces of water in the tablets initiating the reaction between the alkali metal bicarbonate and the aliphatic carboxylic acid. This reaction causes the release of carbon dioxide and water. Where the tablet is hermetically sealed in polythene aluminum foil laminates or other gas tight pack, gas evolution causes the pack to "inflate" and causes deterioration of the tablet and possible degradation of the active ingredient. Thus the inclusion of anhydrous alkali metal carbonate reduces the sensitivity of effervescent tablets to moisture and improves the keeping properties of packed tablets.

Accordingly, the present invention is a process for the preparation of a water soluble chemical composition compounded in an effervescent tablet form, which comprises the direct pressing into tablet form by a direct compression process as hereinbefore defined, of a powder comprising a chemical compound, an alkali metal bicarbonate, an alkali metal carbonate and a solid, water soluble aliphatic carboxylic acid or an acid salt thereof.

The chemical compound may be for example a sterilizing or bactericidal active compound such as a chlorine-containing compound by which is meant a compound which will release chlorine on contact with water or aqueous media. Examples of such compounds are sodium dichloro-s-triazine trione and dichlorodimethyl hydantoin. The chemical compound may also be selected from well known pharmaceutical compounds such as ascorbic acid, paracetamol, codeine and acetylsalicylic acid. It will be understood however, that the invention is not limited to the use of these specific compounds and that any compound which does not give rise to undesirable reactions which the other compounds of the composition may be employed.

The alkali metal bicarbonate may suitably be sodium or potassium bicarbonate. Similarly the alkali metal carbonate may be sodium or potassium carbonate.

The composition may contain other components such as lubricants to aid the formation of tablets having sufficient mechanical stability. Suitable lubricants are for example magnesium stearate or boric acid. Alternatively as is described and claimed in our British Patent Specifications Nos. 1,165,098 and 1,221,038 when the composition contains adipic acid or an acid salt thereof as the acid component, the lubricant substance may be omitted.

The process according to the present invention is described in more detail with reference to the following examples.

EXAMPLE 1

Sodium carbonate as anhydrous powder fine grade is mixed with adipic acid powder, sodium bicarbonate medium coarse and sodium dichloro-s-triazine trione to the following formulation and compressed on a single punch or rotary tablet machine.

|  | per tablet |
| --- | --- |
| Sodium dichloro-s-triazine trione | 500 mg |
| Sodium carbonate anhydrous fine powder | 50 mg |
| Sodium bicarbonate medium coarse | 225 mg |
| Adipic acid | 225 mg |

The resulting tablets were of good physical appearance with a smooth uniform surface and acceptable hardness. On adding to water at 20° C. the tablet effervesced smoothly from the surface and dissolved while maintaining unit form of diminishing size. No "ingredient fall out" phenomenon was observed.

EXAMPLE 2

The following composition was tabletted by direct compression as described in Example 1.

|  | per tablet |
| --- | --- |
| Gibberellic acid | 1000 mg |

-continued

| | per tablet |
|---|---|
| Sodium carbonate powder anhydrous | 500 mg |
| Sodium bicarbonate granules | 5000 mg |
| Adipic acid | 3500 mg |
| Magnesium Stearate | 30 mg |

As in Example 1 the resulting tablets were of good physical appearance with a smooth uniform surface and acceptable hardness.

What we claim is:

1. A process for the tabletting direct from powder form without intervening granulation of a composition containing an active compound having sterilizing, bactericidal or pharmaceutical properties, said tablet producing an effervescent action when contacted with water, the process consisting of direct compression in the absence of substantial wetting of a homogenous powdered admixture consisting essentially of said active compound, an alkali metal bicarbonate for carbon dioxide liberation to generate effervescent action, and a solid, water soluble, aliphatic carboxylic acid or acid salt thereof in the presence of an alkali metal carbonate also in powder form, but not primarily for effervescent action to form a stable, soluble and hard tablet composition.

* * * * *